United States Patent [19]

Kajs et al.

[11] Patent Number: 5,397,573
[45] Date of Patent: Mar. 14, 1995

[54] LAXATIVE COMPOSITIONS

[75] Inventors: Theresa M. Kajs, Loveland; Paul J. Sagel, West Chester, both of Ohio

[73] Assignee: The Procter & Gamble Company, Cincinnati, Ohio

[21] Appl. No.: 72,200

[22] Filed: Jun. 4, 1993

[51] Int. Cl.$^6$ .......................... A61K 1/20; A61K 9/22; A61K 9/52
[52] U.S. Cl. .................................... 424/451; 424/455; 424/457; 424/463; 424/464; 424/474; 424/480; 424/482; 424/195.1; 514/892
[58] Field of Search ............... 424/451, 455, 463, 474, 424/482, 457, 195.1, 464, 480; 514/892

[56] References Cited

U.S. PATENT DOCUMENTS

| | | | |
|---|---|---|---|
| 4,256,875 | 3/1981 | Gabriel et al. | 536/4 |
| 4,402,944 | 9/1983 | Callahan et al. | 424/180 |
| 4,476,121 | 10/1984 | Moss | 424/195 |
| 4,511,561 | 4/1985 | Madaus et al. | 424/195.1 |
| 4,595,592 | 6/1986 | Hietala | 424/195.1 |
| 4,766,004 | 8/1988 | Moskowitz | 426/658 |
| 4,842,865 | 6/1989 | Durr et al. | 424/456 |
| 4,857,331 | 8/1989 | Shaw et al. | 424/440 |
| 5,173,296 | 12/1992 | Andre et al. | 424/195.1 |
| 5,232,699 | 8/1993 | Colliopoulos | 424/195.1 |
| 5,258,181 | 11/1993 | Cregier et al. | 424/195.1 |

OTHER PUBLICATIONS

Perdiem ® (sold by Rorer Consumer Pharmaceuticals), *Physicians' Desk Reference for Nonprescription Drugs*, 10th Edition (Medical Economics Company Inc.; 1989) pp. 666–667.

Ex-Lax ® Choclated Laxative (sold by Sandoz Consumer), *Physicians' Desk Reference for Nonprescription Drugs*, 10th Edition (Medical Economics Company Inc.; 1989), p. 677.

*The Merck Index*, 10th Edition (1983), No. 5662 ("Menthol"), No. 5663 (I–Menthone) and No. 5664 (Menthyl Acetate).

*The Merck Index*, 10th Edition (1983), No. 8298 (Senna) and No. 8299 (Sennoside A&B) "Proceedings, First International Symposium on Senna", *Pharmacology*, 36, Suppl. 1 (Karger; 1988).

*The Lawrence Review of Natural Products*, Topic "Peppermint" (copyright 1990 by Facts and Comparisons.

*British Pharmacopoeia*, "Peppermint Oil", pp. 422–423 (1988).

*National Formulary XVII*, "Peppermint Oil", pp. 1956–1957 (1990).

*Primary Examiner*—Thurman K. Page
*Assistant Examiner*—Amy Hulina
*Attorney, Agent, or Firm*—Douglas C. Mohl; Mary Catherine Poland; Jacobus C. Rasser

[57] ABSTRACT

Laxative compositions containing sennoside and menthol, pharmaceutically-acceptable esters of menthol, or mixtures thereof, preferably as peppermint oil; and methods for treating constipation by orally concurrently administering to the lower gastrointestinal tract of a person in need of such treatment sennoside and menthol.

17 Claims, No Drawings

5,397,573

LAXATIVE COMPOSITIONS

BACKGROUND OF THE INVENTION

The present invention relates to laxative compositions containing sennoside and menthol, preferably as peppermint oil, and the methods for treating constipation by orally concurrently administering to the lower gastrointestinal tract of a person in need of such treatment sennoside and menthol.

The use of senna and sennosides as natural laxatives is known. Negative aesthetics and performance attributes are recognized with using senna-containing laxative compositions. U.S. Pat. No. 4,511,561, issued Apr. 16, 1985, to Madaus et al. reports that undesirable side effects may be observed with the use of sennosides. This U.S. Patent describes certain compositions containing psyllium and senna resulting from a specific granulation procedure. It also describes the use of peppermint oil as a flavor oil.

In spite of this and other work to develop laxative products containing sennosides, there continues to be a need for new compositions which have improved aesthetics and/or reduced undesirable side effects (e.g., reduced cramping and/or reduced gas and/or reduced bloating) and/or improved consumer acceptability to encourage regular compliance for treating constipation; which are in convenient dosage forms; and which are effective as laxatives. It has been discovered by the present invention that the use of higher levels of menthol, preferably as part of peppermint oil, delivered to the lower gastrointestinal tract in combination with sennosides satisfies these needs.

An object of the present invention is therefore to provide menthol/sennoside-containing compositions which have improved aesthetics and/or reduced undesirable side effects to encourage consumer compliance with regular therapeutic use to treat constipation. A further object is to provide convenient dosage forms (especially in unit dosage forms suitable for ingestion by swallowing, such as tablets, caplets and capsules) containing sennosides and menthol and/or menthol esters which are effective for treating constipation. A further object is to provide methods for treating constipation in humans and lower animals by orally concurrently administering to the lower gastrointestinal tract menthol and sennosides.

These and other objects of the present invention will become readily apparent from the detailed description which follows.

All percentages and ratios used herein are by weight unless otherwise specified.

SUMMARY OF THE INVENTION

This invention relates to laxative compositions comprising a safe and effective amount of sennoside, from about 1% to about 99% of menthol, pharmaceutically-acceptable esters of menthol, or mixtures thereof (preferably as peppermint oil), and from about 1% to about 99% carrier materials. Furthermore, it is necessary that the compositions be in a dose form which does not allow all the menthol to come into contact with the stomach, and preferably is a dose form which provides for delivery of the menthol to the lower gastrointestinal tract without substantial availability of the menthol in the stomach, such as by means of swallowable unit dosage forms (e.g., tablets; caplets; capsules) from which most or all of the menthol is released in the lower gastrointestinal tract.

The present invention further relates to methods for treating constipation in humans or lower animals. These methods comprise orally concurrently administering to the lower gastrointestinal tract of the human or lower animal in need of such treatment a safe and effective amount of sennoside and menthol.

DETAILED DESCRIPTION OF THE INVENTION

The present invention relates to menthol/sennoside-containing compositions. These compositions comprise: (a) sennoside; (b) menthol, pharmaceutically-acceptable esters of menthol, or mixtures thereof, preferably as part of peppermint oil. The menthol is present in the compositions in a form which does not allow all the menthol to come into contact with the stomach. Preferred are dose forms whereby most or all of the menthol is released in the lower gastrointestinal tract, thereby limiting the levels of menthol present in the stomach from oral administration of these compositions. This is preferably accomplished by compositions comprising menthol (and/or menthol esters) contained such that the contained menthol is released in the lower gastrointestinal tract, such as by enteric coating or encapsulating or otherwise delaying the release of the menthol from the compositions until it enters the lower gastrointestinal tract. The term "lower gastrointestinal tract", as used herein, means the portion of the gastrointestinal tract including the small intestine and large intestine, preferably the ileum and large intestine.

The components for use in laxative compositions of the present invention, and the amounts preferred to be utilized, are described in detail hereinafter.

(a) Sennoside:

Sennosides are plant-derived compounds that belong to the anthraquinone group of stimulant laxatives. Sennosides are derived from the leaves or pods of various species of the Cassia plant. Commercial sources include the species *Cassia angustifolia* (*Tinnevelly senna*) and *Cassia acutifolia* (*Cassia senna* or *Alexandria senna*). Commercially, sennosides are available as pods, leaves, or concentrates of the leaves and/or pods, and therefore, as used herein, sennosides includes not only the pure or concentrated sennoside compounds having laxative properties but also senna plant materials which have laxative properties.

Frequently sold concentrates range from 3%–95% calcium sennosides. The remaining components in the concentrate also originate from the plant, or are formed during extraction. Sennosides supplied from concentrates of senna pods are preferred. Such concentrates have ranges of sennosides content typically from about 20% to about 90%. Obviously, the higher the sennoside level in such concentrates, the less concentrate needed for the laxative compositions. Sennosides are also described in detail in *The Merck Index*, 10th Edition (1983), No. 8298 ("Senna") and No. 8299 ("Sennoside A&B") and in "Proceedings, First International Symposium on Senna", *Pharmacology*, 36, Suppl. 1 (Karger; 1988), incorporated herein by reference in their entirety. Commercially available sennoside-containing compositions useful for the methods of the present invention are also known, such as Gentle Nature ® Natural Vegetable Laxative (supplied by Sandoz Consumer).

The laxative compositions of the present invention comprise a safe and effective amount of sennoside, which is typically from about 1 mg to about 300 mg per dose, and preferably from about 5 mg to about 100 mg per dose. By weight of the present invention compositions, sennosides therefore typically comprise from about 0.01% to about 75%, and preferably from about 0.1% to about 40%.

(b) Menthol:

The compositions of the present invention also comprise menthol, pharmaceutically-acceptable esters of menthol, or mixtures thereof, preferably as part of peppermint oil. The terms "pharmaceutically-acceptable esters of menthol" and "menthol esters", as used herein, mean those esters of menthol safe for ingestion by humans or lower animals, and which are cleaved in the gastrointestinal tract (by hydrolysis or enzymatically or otherwise) to provide menthol in the lower gastrointestinal tract according to the present invention. Menthol is a well known, commercially available material frequently used for its coolant properties both topically and orally, and as a flavorant. It is described in detail in *The Merck Index*, 10th Edition (1983), No. 5662 ("Menthol"), incorporated herein by reference in its entirety.

Peppermint oil is also a well known, commercially available material which is also used for its coolant properties and as a flavorant. In addition to containing a substantial concentration of free menthol, it also contains menthol esters (e.g., menthol acetate) and menthone. Peppermint oil is described in more detail in *The Lawrence Review or Natural Products*, Topic "Peppermint" (copyright 1990 by Facts and Comparisons); *British Pharmacopoeia*, "Peppermint Oil", pages 422–423 (1988); *National Formulary XVII*, "Peppermint Oil", pages 1956-1957 (1990); and *The Merck Index*, 10th Edition (1983), No. 5663 ("1-Menthone") and No. 5664 ("Menthyl Acetate"); all incorporated herein by reference in their entirety. Peppermint oil is preferred for use in the present invention, and preferred Peppermint Oil comprises at least about 50% total menthol, free and/or as its ester. Commercially available enteric coated peppermint oil compositions useful for the methods of the present invention are also known, such as Colpermin (supplied by Tillotts Laboratories) and Herbal Biotherapy, IBS (supplied by Enzymatic Therapy).

The menthol and/or menthol esters in the compositions and methods of the present invention is used at levels higher than typically used as flavorants or coolants for orally ingested compositions. Such levels may produce gastric upset in certain persons if not delivered by the present invention compositions and methods to minimize the levels of the menthol in the stomach. Therefore the preferred present compositions and methods deliver most or all of the menthol and/or menthol esters to the lower gastrointestinal tract where the menthol is effective for providing the benefits in combination with the sennosides according to the present invention. As noted herein before, this is preferably achieved by coating or encapsulating or otherwise delaying the release of the menthol and/or menthol esters from the compositions or by the present invention methods until it is in the lower gastrointestinal tract.

Compositions of the present invention typically comprise from about 1% to about 99% of menthol, pharmaceutically-acceptable esters of menthol, or mixtures thereof, and preferably from about 5% to about 80%, by weight of the compositions. If peppermint oil is used, the compositions typically comprise from about 1% to about 99% of peppermint oil, and preferably from about 10% to about 95%, by weight of the composition.

(c) Optional Carrier Materials:

In addition to the sennosides and menthol as described hereinbefore, the compositions of the present invention may contain optional carrier materials. The term "carrier materials", as used herein, means one or more compatible solid or liquid filler diluents or encapsulating substances which are suitable for administration to a human or lower animal. The term "compatible", as used herein, means that the components of the compositions are capable of being commingled with the sennosides and menthol, and with each other, in a manner such that there is no interaction which would substantially reduce the laxative efficacy of the present compositions under ordinary use situations. Carrier materials must, of course, be of sufficiently high purity and sufficiently low toxicity to render them suitable for oral administration to the human or lower animal being treated.

The choice of carrier materials to be used in the present compositions is basically determined by the desired form of the composition to be administered. Preferred compositions of the present invention are in unit dosage form suitable for oral ingestion by swallowing, such as tablets, caplets, capsules (including gel caps and liquid-caps) and the like. Carrier materials suitable for the preparation of unit dosage forms for oral administration are well-known in the art. Their selection will depend on secondary considerations like taste, cost, shelf stability, which are not critical for the purposes of the present invention, and can be made without difficulty by a person skilled in the art.

Some examples of substances which can serve as carrier materials are sugars such as lactose, glucose, and sucrose; starches such as cornstarch and potato starch; cellulose and its derivatives such as sodium carboxymethylcellulose, ethylcellulose, cellulose acetate; powdered tragacanth; malt; gelatin; talc; stearic acid; magnesium stearate; dicalcium phosphate; calcium sulfate; vegetable oils such as peanut oil, cottonseed oil, sesame oil, olive oil, corn oil, and oil of theobroma; polyols such as propylene glycol, glycerine, sorbitol, mannitol, and polyethylene glycol; agar; alginic acid; as well as other non-toxic compatible substances used in pharmaceutical formulations. Preferred carrier materials are those substances which act to delay release of most or all of the menthol and/or menthol esters from the compositions useful according to the present invention until the lower gastrointestinal tract, such as enteric coating agents and encapsulating materials (e.g., cellulose acetate phthalate; ethyl cellulose; Eudragit ® coating materials, supplied by Rhom Pharma).

When desired or necessary, suitable binders, lubricants, and disintegrating agents can also be incorporated in the compositions. Suitable binders include starch, gelatin, natural sugars, corn sweeteners, natural and synthetic gums such as acacia, sodium alginate, carboxymethylcellulose, microcrystalline cellulose, polyethylene glycol and waxes. Lubricants may include, for example, boric acid, sodium benzoate, sodium acetate, sodium chloride, etc. Disintegrators include, for example, starch, methylcellulose, agar, bentonite, guar gum, etc. Wetting agents such as sodium lauryl sulfate, as well as coloring agents, flavoring agents, sweetening agents, excipients, tableting agents, stabilizers, antioxidants, and preservatives can also be present. Other compatible pharmaceutical actives, such as NSAID drugs, pain killers, muscle relaxants, and other laxative agents (e.g., fiber materials such as psyllium;

phenolphthalein; bisacodyl; cascara; sagrada; casanthranol) may be included in the carrier materials for use in the compositions of the present invention.

The optional carrier materials if used in the present compositions are used at a concentration sufficient to provide a practical size to dosage relationship. The carrier materials typically comprise from about 1% to about 99%, preferably from about 5% to about 95%, and more preferably from about 5% to about 90%, by weight of the present compositions.

Methods for Treating Constipation

The present invention also relates to methods for treating constipation in humans or lower animals. These methods comprise orally concurrently administering to the lower gastrointestinal tract of the human or lower animal in need of such treatment a safe and effective amount of sennoside and menthol, preferably as peppermint oil. The phrase "orally concurrently administering to the lower gastrointestinal tract", as used herein, means that the sennoside and menthol (as free menthol and/or menthol esters) are both administered orally (either by ingestion of a composition of the present invention or by separate ingestion of a composition containing sennoside and a composition containing menthol) such that the sennoside and menthol are both present in the lower gastrointestinal tract within about the same time period such that they concurrently affect the lower gastrointestinal tract. Ingestion of separate compositions according to this method is preferably within a few hours of each other, more preferably within about one hour of each other, and most preferably within about 10 minutes of each other.

The phrase "safe and effective amount", as used herein, means an amount of the sennoside-containing composition high enough to significantly positively modify the condition being treated, but low enough to avoid serious side effects at a reasonable benefit/risk ratio within the scope of sound medical judgment. The safe and effective amount will vary with the age and physical condition of the patient being treated, the severity of the condition, the duration of treatment, the nature of concurrent therapy, the specific sennoside employed, the carrier materials being employed, and like factors within the knowledge and expertise of the attending physician. However, single dosages of the sennosides can range from about 1 mg to about 300 mg, and preferably from about 5 mg to about 100 mg. Menthol (or the equivalent amount of menthol from menthol esters) is preferably used for single dosages within the range of from about 50 mg to about 1000 mg, and preferably from about 75 mg to about 300 mg (if provided as peppermint oil, single dosages provide peppermint oil within the range of from about 100 mg to about 1000 mg, and preferably from about 200 mg to about 750 mg). Up to about 2-3 single dosages per day may be administered.

The following examples further describe and demonstrate embodiments within the scope of the present invention. The examples are given solely for the purpose of illustration and are not to be construed as limitations of the present invention since may variations are possible without departing from its spirit and scope.

EXAMPLE 1

A swallowable capsule according to the present invention is prepared as follows:

| Components | Weight % |
| --- | --- |
| Sennoside[1] | 5% |
| Peppermint Oil[2] | 83% |
| Capsule[3] | 12% |

[1]57% Sennoside, supplied by Huhtamaki Leiras Corp.
[2]Peppermint oil containing approximately 45% menthol, supplied by A.M. Todd Company.
[3]Gelatin capsules, size 0, coated with cellulose acetate phthalate supplied by Eastman Kodak Company.

These capsules are prepared by mixing the sennoside and peppermint oil, followed by filling the gelatin capsules and sealing with a cellulose acetate phthalate coating to provide 700 mg capsules containing 20 mg sennoside per capsule. Ingestion by swallowing one capsule as needed for constipation by a person in need of such treatment provides fast, well tolerated relief.

EXAMPLE 2

A method for treating constipation in a human in need of such treatment according to the present invention is as follows. A patient in need of treatment ingests (within about 5 minutes of each other) 2 capsules of Colpermin (0.2 ml of peppermint oil per capsule; supplied by Tillotts Laboratories) and 1 tablet of Gentle Nature ® Natural Vegetable Laxative (20 mg of sennoside; supplied by Sandoz Consumer) as need for constipation to provide fast, well tolerated relief.

What is claimed is:

1. A laxative composition comprising:
   (a) from about 0.01% to about 75% of sennoside;
   (b) from about 1% to about 99% menthol, pharmaceutically-acceptable esters of menthol, or mixtures thereof; and
   (c) from about 1% to about 99% carrier material;
   and wherein further the composition is in a dose form which does not allow all the menthol to come into contact with the stomach.

2. The composition according to claim 1 wherein the composition is in a unit dosage form.

3. The composition according to claim 2 wherein the sennoside is present at a level of from about 1ing to about 300 mg per unit dose.

4. The composition according to claim 3 wherein the unit dose form is selected from the group consisting of tablet, capsule, and caplet.

5. The composition according to claim 4 comprising menthol, pharmaceutically-acceptable esters of menthol, or mixtures thereof contained such that the contained menthol is released in the lower gastrointestinal tract.

6. The composition according to claim 1 comprising peppermint oil.

7. The composition according to claim 3 wherein the sennoside is present at a level of from about 5 mg to about 100 mg per unit dose.

8. The composition according to claim 7 wherein the unit dose form is selected from the group consisting of tablet, capsule, and caplet.

9. The composition according to claim 8 comprising enteric coated or encapsulated menthol such that this menthol is released in the lower gastrointestinal tract.

10. The composition according to claim 7 comprising peppermint oil.

11. A laxative composition comprising:
    (a) from about 0.1% to about 40% sennoside;
    (b) from about 10% to about 95% peppermint oil; and (c) from about 5% to about 90% carrier material; and wherein further the composition is in a dose form whereby most or all of the peppermint oil is released from the composition in the lower gastrointestinal tract.

12. The composition according to claim 11 in a unit dose form selected from the group consisting of tablet, capsule, and caplet.

13. The composition according to claim 12 wherein the sennoside is present at a level of from about 5 mg to about 100 mg per unit dose.

14. The composition according to claim 13 comprising enteric coated or encapsulated peppermint oil such that this peppermint oil is released in the lower gastrointestinal tract.

15. A method for treating constipation in a human or lower animal, said method comprising orally concurrently administering to the lower gastrointestinal tract of the human or lower animal in need of such treatment from about 0.01% to about 75% of sennoside and from about 1% to about 99% of menthol.

16. The method according to claim 15 comprising administering to the lower gastrointestinal tract from about 5 mg to about 100 mg sennoside, and from about 50 mg to about 1000 mg menthol.

17. The method according to claim 15 comprising administering to the lower gastrointestinal tract from about 5 mg to about 100 mg sennoside, and from about 100 mg to about 1000 mg peppermint oil.

* * * * *

UNITED STATES PATENT AND TRADEMARK OFFICE
CERTIFICATE OF CORRECTION

PATENT NO. : 5,397,573

DATED : March 14, 1995

INVENTOR(S) : THERESA MARIE KAJS, ET AL.

It is certified that errors appear in the above-identified patent and that said Letters Patent is hereby corrected as shown below:

Column 6, line 43, "ling" should be --1 mg.--.

Signed and Sealed this

Twenty-seventh Day of June, 1995

BRUCE LEHMAN

Attest:

*Attesting Officer*        *Commissioner of Patents and Trademarks*